United States Patent
Lefesvre

(12) 
(10) Patent No.: US 6,415,201 B1
(45) Date of Patent: Jul. 2, 2002

(54) PROCESS AND SYSTEM FOR MANAGEMENT OF BATCHES OF COMPONENTS OF THE HAEMATOPOIETIC SYSTEM FOR DEFERRED USE

(75) Inventor: Andre Lefesvre, 7, rue Washington, F-75008 Paris (FR)

(73) Assignees: Andre Lefesvre, Paris; Patrick Rambaud, Fontaine le Port, both of (FR)

( * ) Notice: Subject to any disclaimer, the term of this patent is extended or adjusted under 35 U.S.C. 154(b) by 0 days.

(21) Appl. No.: 09/118,857

(22) Filed: Jul. 20, 1998

Related U.S. Application Data

(63) Continuation of application No. PCT/FR98/00708, filed on Apr. 8, 1998.
(60) Provisional application No. 60/084,672, filed on May 7, 1998.

(51) Int. Cl.$^7$ .......................... G06F 7/00; G06F 159/00; A61M 1/00; A61B 19/00
(52) U.S. Cl. .................. 700/214; 700/213; 700/315; 705/2; 705/3; 604/317; 604/408
(58) Field of Search .................. 705/2, 3, 28; 700/213, 700/214, 215; 604/6.01, 317, 408

(56) References Cited

U.S. PATENT DOCUMENTS

| | | | | |
|---|---|---|---|---|
| 4,804,363 A | * | 2/1989 | Valeri ............................. | 604/6 |
| 4,923,797 A | * | 5/1990 | Babior ........................... | 435/2 |
| 5,004,681 A | * | 4/1991 | Boyse et al. .................... | 435/2 |
| 5,133,703 A | * | 7/1992 | Boehringer et al. ......... | 604/317 |
| 5,915,240 A | * | 6/1999 | Karpf ............................ | 705/2 |
| 6,157,914 A | * | 12/2000 | Seto et al. ...................... | 705/3 |

FOREIGN PATENT DOCUMENTS

| | | |
|---|---|---|
| DE | 34 21 011 | 12/1985 |
| WO | WO 89/04168 | 5/1989 |
| WO | WO 94/00567 | 1/1994 |

* cited by examiner

*Primary Examiner*—Jeffrey Gaffin
*Assistant Examiner*—Chun Cao
(74) *Attorney, Agent, or Firm*—Young & Thompson

(57) ABSTRACT

Process for management of batches of haematopoietic-system components belonging to human subjects from whom these batches have been collected for deferred use. Each batch of haematopoietic-system components associated with a subject is packed and stored in a cryogenic storage site among a plurality of cryogenic storage sites ($S_A$, ... $S_L$) and then transferred on request from this storage site to a cell treatment center for re-use on said subject or on said subject's parent. A gathering of both personal data relating to the subject from whom the batch was collected and of data relating to the collection is associated with each collection phase (I).

10 Claims, 3 Drawing Sheets

FIG_1

PROCESS AND SYSTEM FOR MANAGEMENT OF BATCHES OF COMPONENTS OF THE HAEMATOPOIETIC SYSTEM FOR DEFERRED USE

CROSS-REFERENCE TO RELATED APPLICATIONS

This application is a continuation of international application PCT/FR98/00708 filed on Apr. 8, 1998, which designates the United States of America.

This application also claims the benefit of U.S. Provisional Application No. 60/084,672 filed on May 7, 1998.

The present invention relates to a process for management of batches of components of the haematopoietic system, particularly lymphocytes, monocytes, marrow, serum, plasma, for deferred use. It also relates to a management system for using the process according to the invention.

BACKGROUND OF THE INVENTION

Scientific and clinical works have demonstrated the therapeutic qualities of auto-use of lymphocyte and monocyte derivatives which helps, in particular, to increase cell immunity.

A promising application of this therapeutic method relates to the possibility of strengthening the immunity of a patient at a time in his life when this strengthening proves to be necessary or vital, or to maintain this immunity throughout his life.

However, a significant difficulty to be overcome lies in the availability of haematopoietic-system components of a patient over periods of time which could be between several months and several decades. Techniques of cryogenic storage for the future which are widely used in several fields of human and animal biology are already known. In particular, banks have been established for preservation and storage of biological elements.

Nevertheless, the current infrastructures and methods regarding storage and management of biological batches are not suitable for the specific application of auto-injection deferred in the long term.

SUMMARY OF THE INVENTION

The object of the present invention is to remedy these disadvantages by proposing a process for management of batches of haematopoietic-system components collected and preserved for deferred use, which gives the users a guarantee of storage and availability in the long term. This object is achieved by a process for management of batches of haematopoietic-system components belonging to human subjects from whom these batches have been collected for deferred use.

According to the invention, each batch of haematopoietic-system components associated with a subject is packed and stored in a cryogenic storage site among a plurality of cryogenic storage sites and then transferred on request from this storage site to a cell treatment center for re-use on said subject or on said subject's parent, and a gathering of both personal data relating to the subject from whom the batch was collected and of data relating to the collection is associated with each collecting phase.

Such a process thus provides patients with the guarantee of storage of their lymphocytes in the long term, with the prospect of having them available at any time for, inter alia, strengthening of their immune system. It therefore becomes possible to give back to people their former immunity and to transmit a cell immunity under rational and reliable management conditions, and also to have access to their corresponding genetic code at the time of collection of the blood.

Preferably, at the end of a collection phase, the lymphocytes collected are packed in the form of a plurality of batches of lymphocytes. This allows flexible and efficient management of re-injections, without the fear of having to thaw a batch of lymphocytes in an excess amount with respect to the needs at that point in time.

In an advantageous embodiment of the process according to the invention, the batches of haematopoietic-system components are stored in several geographically distinct cryogenic storage sites. The object of this characteristic is to increase the safety of the preservation of the haematopoietic-system components collected.

More generally, in the management process according to the invention, the idea of deferred use covers both the field of auto-use in the form, in particular, of auto-injection, use of transfer factor obtained from the lymphocyte collections, or use of monocytes, or use of a culture of lymphocytes with growth factors, such as interleukin II, and the field of use of filiation, in particular in gene therapy, in particular reading of the genetic code and the use of haematopoietic-system components collected from the parents.

The batches of haematopoietic-system components may be re-used, for example, after cell culture in the presence of cell mediators, such as interleukin II, for therapeutic purposes.

According to another aspect of the invention, a system for management of collections of haematopoietic-system components using the process according to the invention is proposed, characterized in that it comprises:

a plurality of centers for collection and packing of batches of haematopoietic-system components, a plurality of cryogenic storage sites provided to receive the batches of haematopoietic-system components, a plurality of centers for cell treatment with batches of haematopoietic-system components, and a center or centers for management of batches of haematopoietic-system components connected by communication means to the collection centers, to the cryogenic storage sites and to the cell treatment centers.

Preferably, the management center or centers cooperate with an express logistics center for forwarding the batches of haematopoietic-system components from the cryogenic storage sites to the cell treatment centers.

Furthermore, the management system according to the invention also comprises means for gathering personal data relating to the patients who have undergone collections of haematopoietic-system components in the plurality of collection centers.

Other details and advantages of the invention will also become apparent in the description below. Regarding the attached drawings, given as non-limiting examples:

DETAILED DESCRIPTION OF THE PREFERRED EMBODIMENTS

Figure 1:
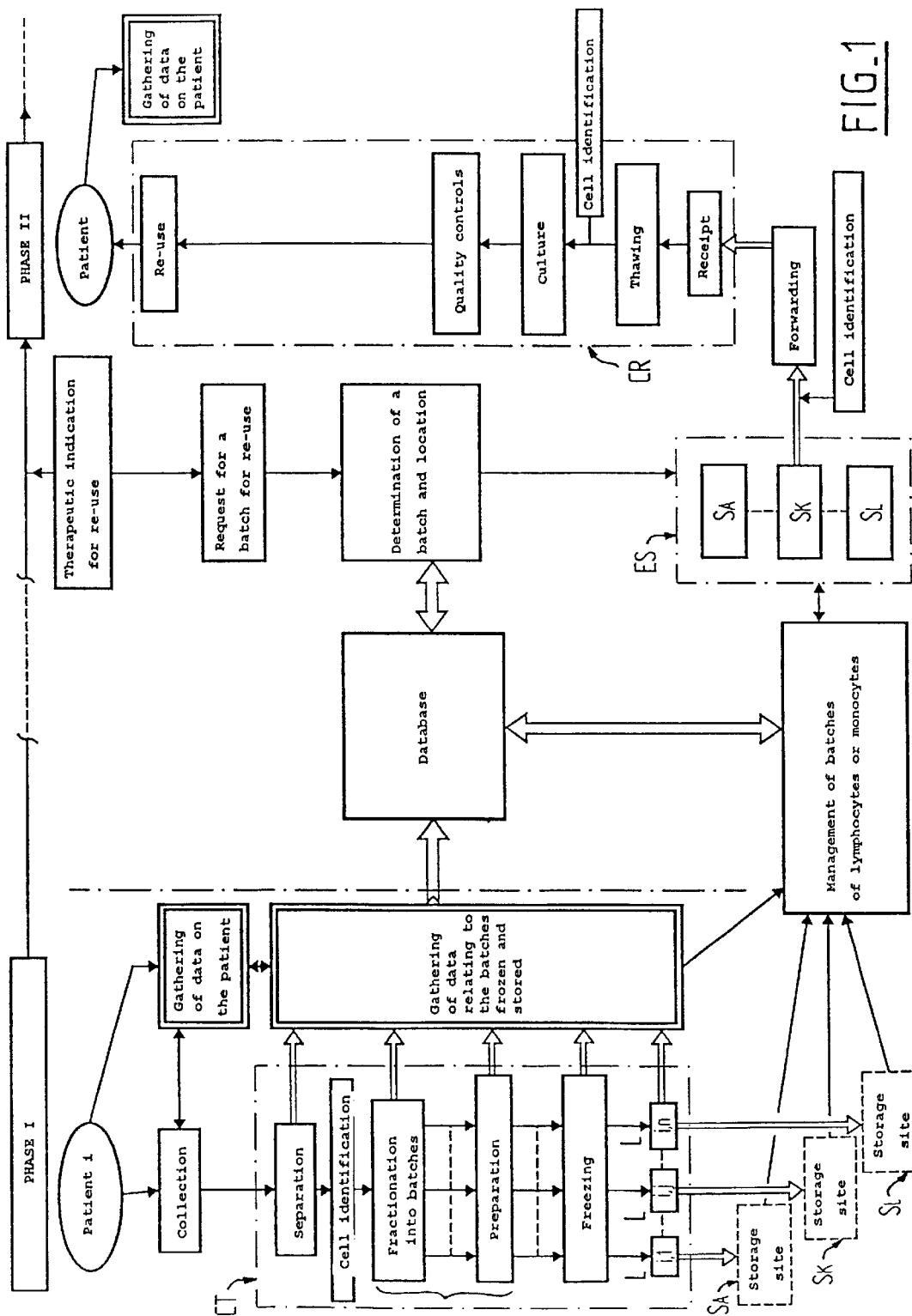
FIG. 1 is a block diagram of the process and system for management of lymphocyte collections according to the invention.

An example of the use of the process for management of collections of haematopoietic-system components, for example lymphocytes or monocytes, and also the corresponding management system, will now be described with reference to FIG. 1.

A first phase I relates to collection and realization of lymphocyte or monocyte batches.

The following stages are carried out during a phase I realized in a specialized center CT:

gathering of data, in particular data relating to the tissue group and information relating to a patient i, collection of blood from this patient, treatment of the blood collected and separation of the lymphocytes and/or monocytes, cell identification, fractionation to obtain a group of batches of lymphocytes and/or monocytes, preparation of the lymphocytes and/or monocytes, including, inter alia, any dehydration, freezing and cryogenic storage of n batches of lymphocytes and/or monocytes $L_{i,1}$, $l_{i,j}$, $l_{i,n}$ in a suitable refrigeration system, for example in a gaseous refrigeration atmosphere.

It should be noted that the separation and fractionation operations may be integrated and carried out within one cytopheresis apparatus. Furthermore, the stage of cell identification, which can use various known identification techniques, may be involved at other stages of phase I, depending on the specific technical features.

The frozen batches of lymphocytes and/or monocytes are then distributed among various storage sites or banks $S_A$, $S_K$, $S_L$. The stocks of batches of lymphocytes are secured and managed. This management uses a database fed with data gathered during each collection and storage phase I. The batches of haematopoietic-system components could thus be stored over widely varying periods, which can range from a few days to several decades, provided that proper storage of the haematopoietic-system components in the long term is guaranteed. Furthermore, the principle of not storing all the batches of one patient at the same site contributes substantially to the security of the supply.

When a therapeutic indication regarding a patient having the benefit of this management process specifies use of haematopoietic-system components, phase II of the process is then undertaken. The process management company is contacted and receives a request for a batch of lymphocytes and monocytes stored and managed on behalf of this patient. By interrogation of the database, a batch belonging to this patient is determined and located in one of the storage sites $S_A$, $S_K$, $S_L$ of all the sites ES. After location and cell identification, the batch in question is forwarded by express transport to a cell treatment center CR, which can also be the center in which the initial collection was made.

The re-use (for example re-injection) phase comprises, for example:

receipt of the batch, including an identification control, which may comprise, in particular, reading of a barcode and a tissue group, thawing of the batch, another cell identification, resuspending the haematopoietic-system components in a culture medium, operations for control of the quality and safety, and re-use of the lymphocytes in the patient.

At the time of this re-use phase II, new data relating to the patient can be gathered again for the purposes of studies and statistical analyses.

Figure 2:
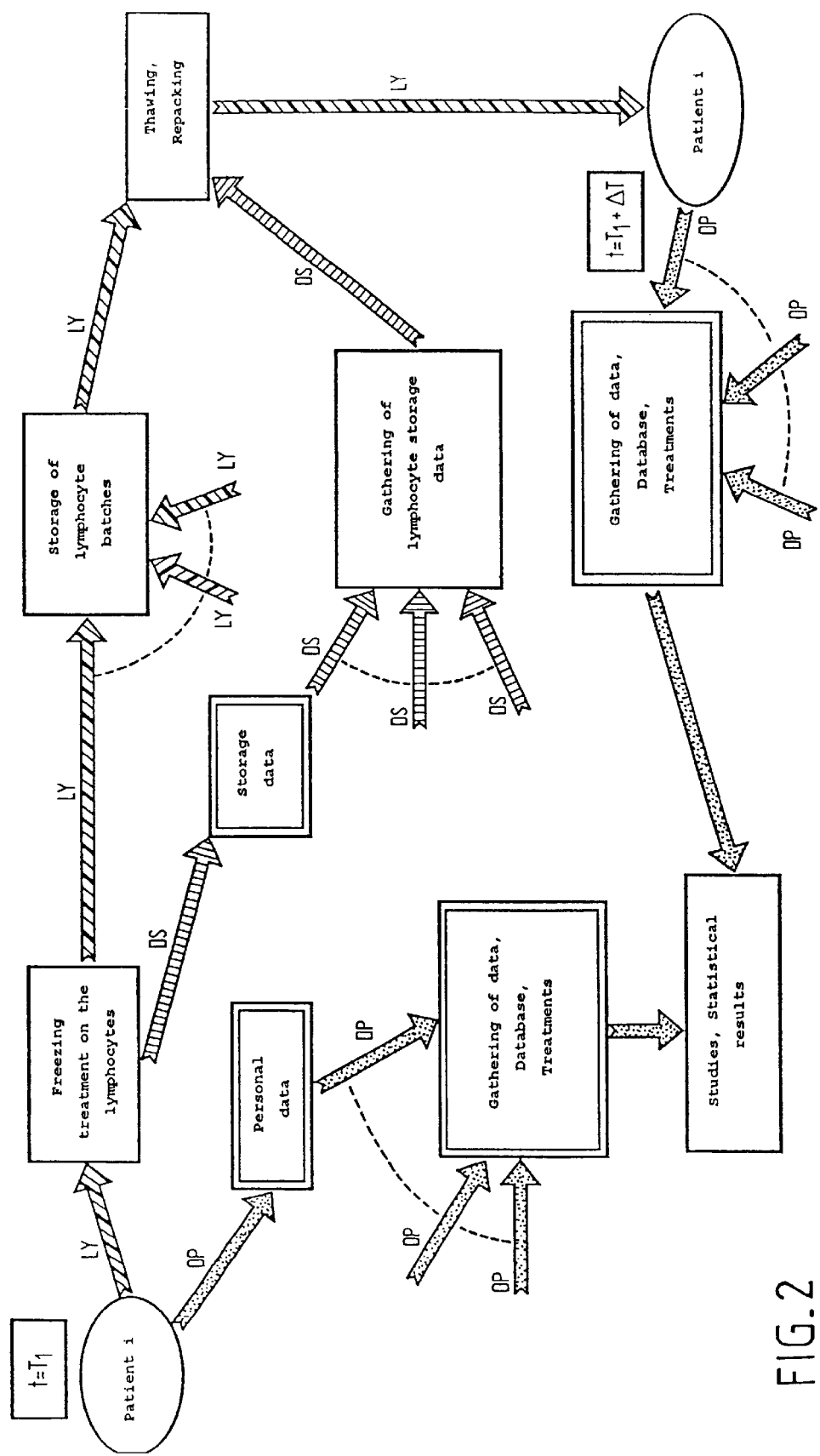
FIG. 2 illustrates the respective flows of collections, personal data and management data resulting from the use of the management process according to the invention.

The management process will -now be described in flow terms, with an analysis of transfers of biological elements, personal data and data relating to collection and storage, with reference to FIG. 2. From any patient calling on the services of a collection management company at a time T1, the following transfers are effected:

transfer of biological elements consisting of the lymphocytes LY or monocytes collected and separated, transfer of personal data DP gathered at the time of collection, subject to observance of the particular legal requirements of each country, transfer of data and parameters directly associated with the collections and essential for management of the collection stocks.

Each of these types of transfer lead to gathering processes:

gathering of batches of haematopoietic-system components with centralized management and various storage sites, gathering of personal data to enter into the statistics databases, and gathering of collection data to establish a database for management of the batches of haematopoietic-system components.

When a re-use phase II, for example in the form of a re-injection, is decided on at a time TI+ΔT, the following transfers are carried out:

transfer of a batch of haematopoietic-system components from a storage site to a cell treatment center, transfer of data and parameters associated with this batch, and transfer of updated personal data on this patient, which are gathered at the time of the re-use phase.

Figure 3:
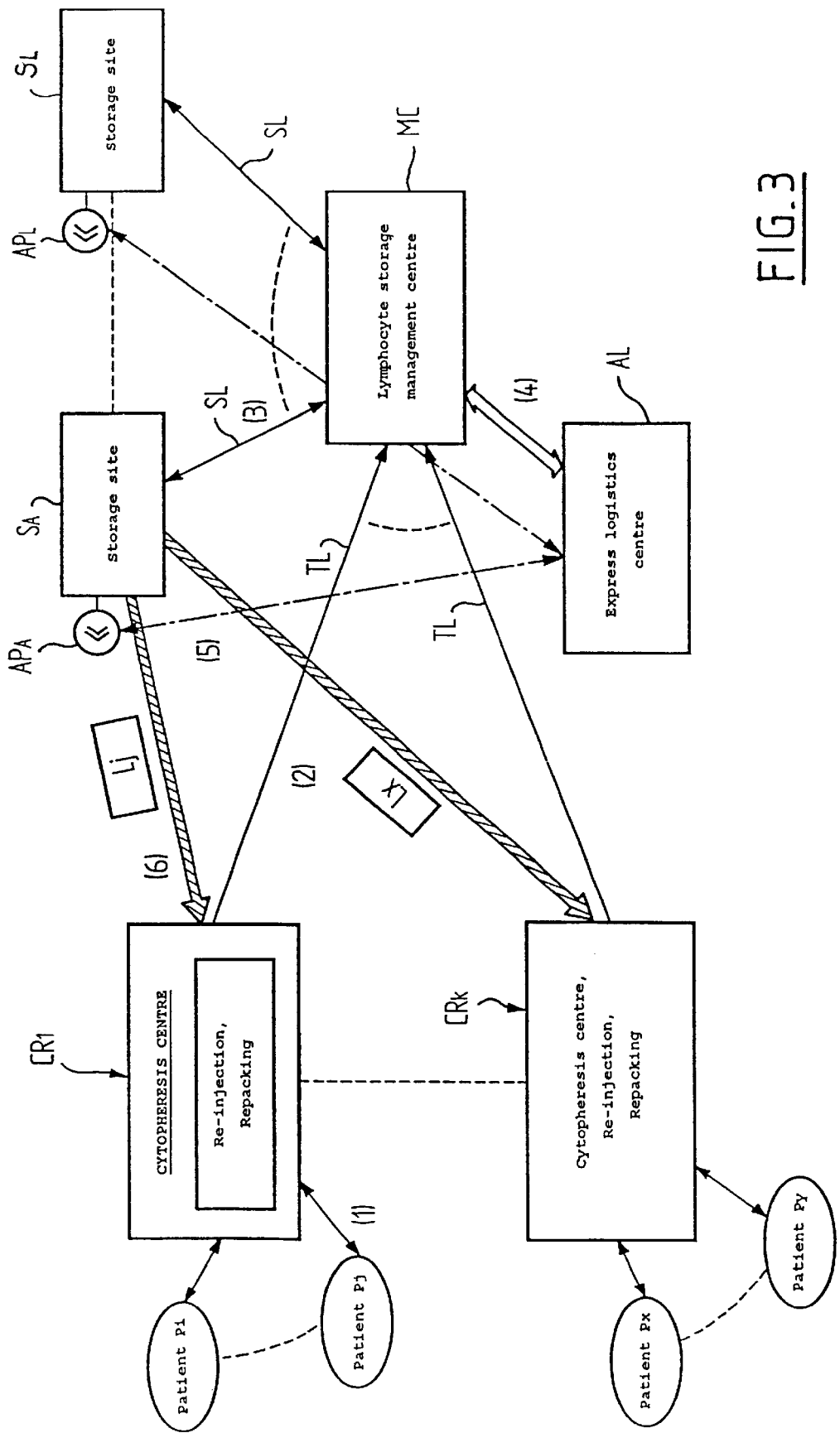
FIG. 3 illustrates the relationships between sites of re-injection, storage and management within a management system according to the invention.

The conditions for carrying-out a re-use phase in the context of the management process according to the invention will now be described, more particularly in terms of the geographical location and logistics, with reference to FIG. 3.

In a given territory, which may be a continent, a country, a region or an urban community, cytopheresis or lymphocyte treatment centers $CR_1$, $CR_K$ are established. These centers, provided to receive patients Pi, Pj, Px, Py who have followed a collection/re-use program using the management process according to the invention, are in communication by connection means TL, such as communication networks which are closed or open (Internet), with one of the centers MC for management of the stores of lymphocytes or monocytes, which may be located at any point on the globe. This management center MC is in permanent communication by suitable means of communication $S_L$ (specialized connections or open network, such as the Internet) with all the storage sites $S_A$, ... $S_L$. Furthermore, the management center MC co-operates with an express logistics center AL connected to express logistics platforms $AP_A$, ... $AP_L$ close to which the storage sites are preferably established. As an example of the use of the management process according to the invention, a patient j contacts (1), on a medical indication, a cytopheresis or re-use center $CR_1$ of his choice, for example the center closest to him. The cell treatment center $CR_1$ consults the management center MC on a terminal connected to it, and transmits (2) to it a request for a batch. The management center MC interrogates the management database and locates a batch of lymphocytes or monocytes $L_j$ corresponding to this patient in one of the storage sites. In the case of diversified multiple storage, the storage site closest to the cell treatment center $CR_1$ is chosen. The management center MC transmits (3) the request to the storage site selected $S_A$ and contacts (4) the express logistics center AL. The storage site $S_A$ then extracts the batch in question and immediately transmits it to the express dispatch platform $AP_A$, which has been activated (5) beforehand by the express logistics center AL. The batch Lj is then forwarded (6) by the express means available, preferably by airplane, to the cell treatment center destination $CR_1$.

It should be noted that each patient following such a program generally has available a stock of batches of haematopoietic-system components, which enables him, for example, to spread successive auto-uses, for example in the form of auto-injections, over a period of time, with the aims of strengthening the immune system or gene or other therapy, or also to use them massively if the stock of haematopoietic-system components made up in this way is required.

The management process according to the invention is preferably implemented in the form of software installed on management and data processing systems, which may be located in batch management centers and be connected to all the data processing sites located within the cytopheresis, express logistics and storage centers.

The invention is of course not limited to the examples which have just been described, and several modifications may be made to these examples without going beyond the context of the invention. In the context of the collection and re-use phases, additional technical stages can thus be provided, according to medical requirements and safety constraints. The means of communication used between the various operational and management centers can be of any nature.

Furthermore, the data gathered in the context of the management process according to the invention may advantageously be processed for statistical purposes, with applications in the field of prevention and insurance.

What is claimed is:

1. A process for management of components of the haematopoietic system belonging to human subjects from whom these components have been collected for deferred use, the process comprising the steps of:

after collection of plural batches of components of the haematopoietic system from a single subject, packing and storing the plural batches of haematopoietic-system components associated with the subject in plural different cryogenic storage sites; and gathering in a single, centralized management data base at a single center for management personal data relating to the subject and batch data relating to locations of the plural batches from the subject and the collection of the plural batches, including cell identification and tissue group; and for a reuse of the plural batches by the subject, on request from a cell treatment center where the subject is to reuse one of the plural batches, interrogating the management data base at the center for management to localize one of the plural batches at one of the cryogenic storage sites; and transferring the one of the plural batches from the one of the cryogenic storage sites to the requesting cell treatment center as directed by the center for management.

2. The process according to claim 1, wherein after collection the haematopoietic-system components collected are fractionated.

3. The process according to claim 1, wherein the batches of haematopoietic-system components are reused as auto-injections.

4. The process according to claim 1, wherein the batches of haematopoietic-system components are reused to produce transfer factors.

5. The process according to claim 1, wherein the batches of haematopoietic-system components are reused on a parent of a collected subject, in view of gene therapy.

6. The process according to claim 1, wherein the batches of haematopoietic-system components are reused after cell culture in presence of cellular mediators for therapeutic purposes.

7. A system for management of collections of haematopoietic-system components, comprising:

a plurality of centers for collection and packing of plural batches of haematopoietic-system components from a single subject;

a plurality of different cryogenic storage sites that each receive ones of the plural batches of haematopoietic-system components from the subject;

a plurality of centers for cell treatment with the plural batches of haematopoietic-system components;

a single centralized management data base containing data identifying the plural batches, the subject, and data related to collection of the plural batches including cell identification and tissue group; and the centralized management data base being located at a single center for management of the plural batches of haematopoietic-system components that is connected by communication means to said center for collection, to said cryogenic storage sites, to said management data base, and to said centers for cell treatment, said center for management localizing the plural batches based on information from said management data base and transferring one of the localized batches from one of said cryogenic storage sites to one of said centers for cell treatment where the subject is to reuse the one of the plural batches.

8. The system according to claim 7, wherein said center for management co-operates with an express logistics center for forwarding the batches of haematopoietic-system components from said cryogenic storage sites to said cell treatment centers.

9. The system according to claim 7, further comprising means for gathering personal data relating to patients who have undergone collections of haematopoietic-system components in said centers for collection.

10. The system according to claim 7, wherein each of said storage sites is connected to an express logistics platform.

* * * * *